United States Patent [19]

Buras

[11] Patent Number: 4,693,243
[45] Date of Patent: Sep. 15, 1987

[54] CONDUIT SYSTEM FOR DIRECTLY ADMINISTERING TOPICAL ANAESTHESIA TO BLOCKED LARYNGEAL-TRACHEAL AREAS

[76] Inventor: Sharon Y. Buras, 713 Live Oak, Metairie, La. 70005

[21] Appl. No.: 844,110

[22] Filed: Mar. 26, 1986

Related U.S. Application Data

[63] Continuation-in-part of Ser. No. 458,074, Jan. 14, 1983, abandoned.

[51] Int. Cl.⁴ .............................................. A61M 25/00
[52] U.S. Cl. .................................. 128/207.15; 604/96; 604/101; 604/265
[58] Field of Search ...................... 128/207.15; 604/96, 604/101, 265

[56] References Cited

U.S. PATENT DOCUMENTS

| | | | |
|---|---|---|---|
| 3,173,418 | 3/1965 | Baran | 128/207.15 |
| 3,394,705 | 7/1968 | Abramson | 604/96 |
| 4,327,721 | 5/1982 | Goldin et al. | 128/207.15 |
| 4,417,576 | 11/1983 | Baran | 128/207.15 |

Primary Examiner—C. Fred Rosenbaum
Assistant Examiner—Sherri E. Vinyard
Attorney, Agent, or Firm—C. Emmett Pugh

[57] ABSTRACT

A flexible, non-collapsible conduit system separable but positioned around a standard cuffed, endotracheal tube to allow for direct topical application of medicinal substances to tissues of the larynx and trachea that might be irritated, traumatized, or stimulated by the endotracheal tube. An external injection port and tubing connect to an internal passage in the endotracheal tube side wall, the passage extending to connect with a system of flexible, non-collapsible conduits, whose lumens are always patent, integrated and distributed above, about and below the cuff area of the endotracheal tube. This system of flexible, non-collapsible conduits are perforated to allow for infusion of topically applied medicinal substance(s), such as anesthetic or anti-inflammatory substances, directly onto those tissues so affected by the cuff and tube regardless of whether the endotracheal tube is completely inflated, partially inflated or completely deflated.

12 Claims, 13 Drawing Figures

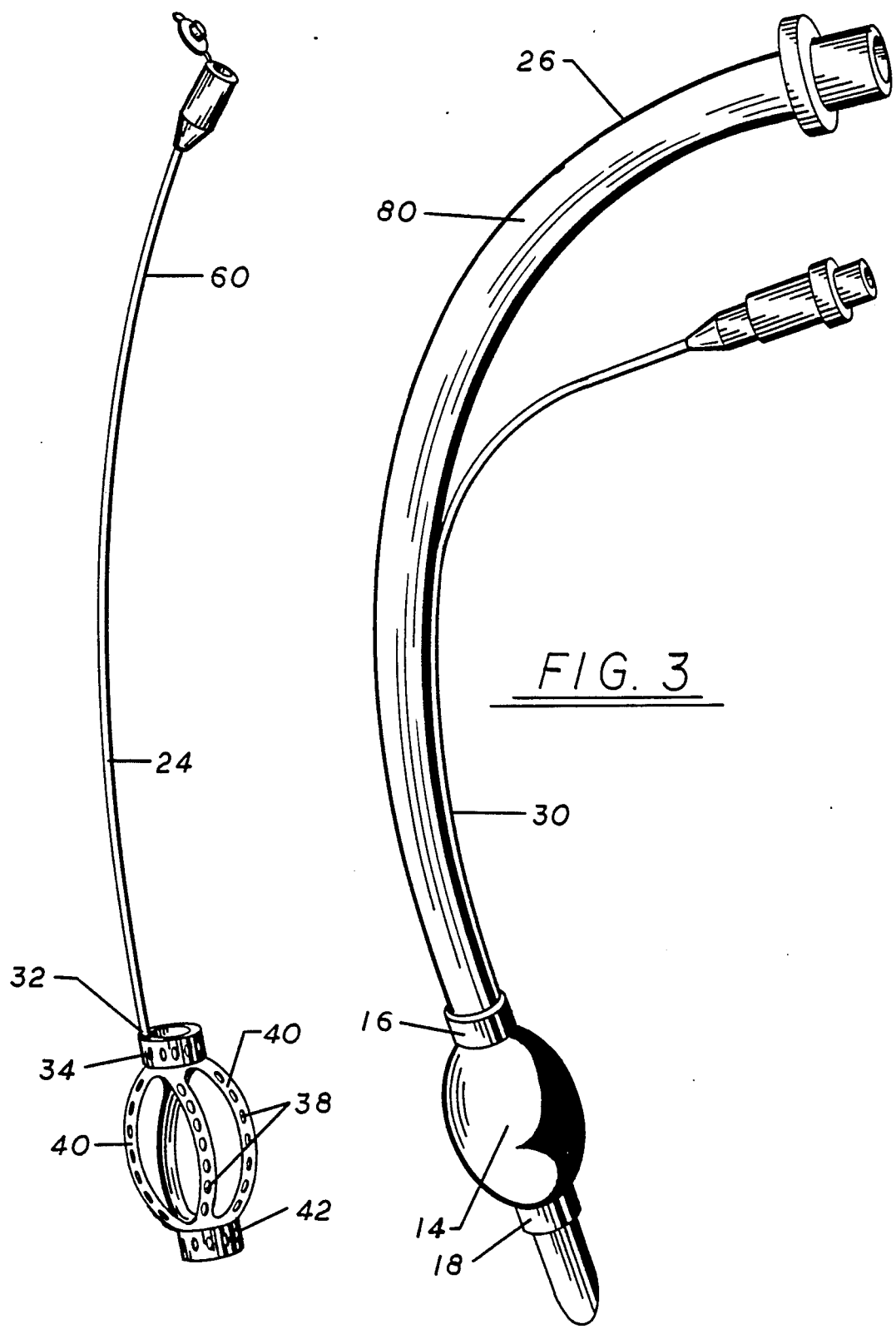

CONDUIT SYSTEM FOR DIRECTLY ADMINISTERING TOPICAL ANAESTHESIA TO BLOCKED LARYNGEAL-TRACHEAL AREAS

REFERENCE TO RELATED APPLICATION

This application is a continuation-in-part of Ser. No. 458,074 filed Jan. 14, 1983 abandoned entitled "Apparatus for Directly Administering Topical Anesthesia . . . ".

BACKGROUND OF INVENTION

1. Field of Invention

The present invention relates generally to the use of balloon, cuffed, endotracheal tubes, providing a device that allows application of medicinal substance(s) directly onto tissue surfaces otherwise blocked, obstructed or irritated by contact or compression of the tissue surfaces by inflation of the balloon cuff of the endotracheal tube.

2. Prior Art and General Background

In the course of surgical operations, indeed in the care of any critically ill person, it is often necessary to intubate the larynx and trachea to provide for stable and secure ventilation of that patient. Such intubation is usually accomplished with a hollow tubular device which allows for direct administration of oxygen or anesthetic gases directly into the respiratory system of the patient. Successful use of such endotracheal tube requires the generation of sufficient pressure in the oxygen or anesthetic gas to promote inflation of the lung and diffusion of the oxygen or gas through the lung tissue.

To promote the generation of sufficient pressure within the airway, most standard endotracheal tubes are equipped with a balloon cuff device, which when distended (inflated) effects a seal with the tissue of the trachea wall, which prevents the loss of such lung-inflating pressures, or loss of necessary oxygen or anesthetic gas.

It is the complications associated with the use of such balloon-cuffed endotracheal tubes to which the present invention is specifically addressed.

Balloon cuffed endotracheal tubes are replete with complications, complications which are unavoidable given the necessity that, in order to function, such balloon-cuffed, endotracheal tubes, when inserted, necessarily make incidental contact with the trachael wall, or, when inflated, must remain in direct, continuous contact with the tissue of the tracheal wall to sustain an effective seal. These tissues are exquisitely sensitive to the effects of direct touch. Such tissues maintain nervous system reflexes to sense even the slightest touch, as to the body such touch would suggest a developing obstruction of the trachea, an event which would threaten the free flowing respiration necessary to sustain life.

The body then interprets the insertion of an endotracheal tube, and especially the inflation of the balloon cuff, as a threat to free respiration. Resultant reflexes initiate coughs, muscular spasms (bucking), cardiac arrhythmias with potential heart stoppage, vomiting, or respiratory depression, all of which threaten the life of the patient.

To prevent these dangerous reflex responses, various methods may be employed. The level of general anesthesia may be deepened, additional narcotic agents may be administered, or the patient may be paralyzed with muscle relaxant agents. Alternatively, topical anesthetics may be applied directly to the larynx and trachea by spraying then through the patient's mouth just prior to intubation. The former methods greatly increase the risk to the patient, while the latter, albeit effective, is only temporary and usually fades away after fifteen to thirty minutes. Heretofore there has been no effective way to reanesthetize the laryngo-trachael area in immediate contact with the endotracheal tube and balloon cuff, without dangerous deflation of the balloon cuff or removal of the cuffed endotracheal tube entirely. Since some surgical and anesthetic procedures require that irritation and touch responses be blocked during the entire operation, or at least during the conclusion thereof, a new approach is required to accomplish this.

The present invention thus supplies a device and method to suppress these potentially hazardous tissue responses and reflexes, and yet minimizes the chances of complications by providing direct and continuous access to those tissues of the body immediately in contact with the endotracheal tube and its distending (inflated) balloon cuff.

Furthermore, the longer the endotracheal tube remains inserted into the larynx and trachea, the greater the potential exists for tissue damage from direct compression and resultant ischemic changes with pressure necrosis. Medical patients maintained in critical care areas of hospitals, or patients undergoing complicated surgery, often remain intubated for extended periods of time. Occasional deflation of the endotracheal tube cuff may be necessary to provide relief from pressure on the tracheal tissue or to remove accumulated body secretions at or below the cuff.

Until the present invention no effective device existed which would allow such cuff deflation without sacrificing access to those areas affected by the cuff or removing the endotracheal tube entirely.

The present invention supplies a device and method to allow these therapeutic options and yet minimize the chance of complications by providing direct and continuous access to those tissues of the body regardless of the state of inflation of the balloon cuff, as well as during various manipulations of the endotrachael tube itself.

In the parent application the following prior patents were cited:

| U.S. Pat. No. | Patentee(s) | Issue Date |
|---|---|---|
| 3,173,418 | Baran | March 1965 |
| 3,394,705 | Abramson | July 1968 |
| 4,327,721 | Goldin et al | May 1982 |
| 4,417,576 | Baran | November 1983 |

In the Baran U.S. Pat. No. 4,417,576 openings for injecting medical substances are included as an integral part of the inflatable balloon-type cuff, which has a spongelike outer wall. Thus, when the cuff is deflated, the openings or lumens likewise completely collapse, causing the operability of the injection system to be dependent on the state of the balloon-type cuff.

In the earlier, Baran U.S. Pat. No. 3,173,418, the injection system is included as a balloon-like arrangement having no significant capability of being structurally self supporting. Thus, when the inflating pressure is removed, it falls down to a flat state.

In contrast, the present invention utilizes a conduit system which, although preferably flexible, also is self-supporting and does not completely collapse when the ballooning pressure in the cuff is removed, maintaining the lumens always patent. Additionally, medical substances are supplied through a sub-system of separated, self-supporting, conduits and not from a largely open area as in the balloon injector of the Baran U.S. Pat. No. 3,173,418.

Additionally, applicant is aware of the additional prior patent and publications—U.S. Pat. No. 4,305,392 issued Dec. 15, 1981, to Martin E. Chester entitled "Endotracheal Tube with Suction Device;" *Principles of Anesthesiology,* (2nd ed.) Vicent J. Collins, Lea & Febiger (Philadelphia) 1976, pp. 343–345, 347, 379, 387 and 1605; and *Anesthesiology,* Vol. 21, No. 6, November–December 1960, p. 775; the latter two of which discuss endotracheal tube cuffs and their structures and characteristics. In the Chester patent, although medicinal fluids are introduced, the only injection service provided is proximal.

Additionally, applicant has previously been recognized as being inventive, having been issued U.S. Pat. No. 4,230,108 on Oct. 28, 1980, on an "Apparatus and Method for Sealing Esophageal Entrance to Trachea Above and Below."

3. Summary, General Discussion of the Invention

It is thus a basic object of the present invention to provide a new and unique, separable or integral, flexible, yet self-supporting and non-collapsible conduit system incorporated around a balloon-cuffed endotracheal tube (ETT) to provide access via perforations in the conduit system for topically applying medicinal substance(s), such as topical anesthetic irrigation to those laryngotracheal area blocked, occluded or compressed by the endotracheal tube and its balloon cuff regardless of the disposition of the ETT.

The present invention utilizes a series of non-collapsible conduits and retains its function independent of the state of operation of the standard endotracheal balloon cuff. By a non-collapsible conduit is meant a conduit whose lumen is always patent regardless of the position or state of operation of the system. The system remains unaffected by environmental pressure changes due to the non-collapsible nature of the conduits, yet maintains flexibility about the balloon cuff to facilitate the ease of insertion and removal by the operator.

BRIEF DESCRIPTION OF THE DRAWINGS

For a further understanding of the nature and objects of the present invention, reference should be had to the following detailed description, taken in conjunction with the accompanying drawings in which like parts are given like reference numerals and wherein:

FIG. 2 is a perspective view of the preferred embodiment of FIG. 1 of the flexible, non-collapsible conduit system of the present invention by itself illustrated separately from the standard cuffed endotracheal tube.

FIG. 3 is a perspective view of the standard, prior art cuffed endotracheal tube of FIG. 1 by itself.

DETAILED DESCRIPTION OF THE PREFERRED, EXEMPLARY EMBODIMENT(S)

Figure 1:
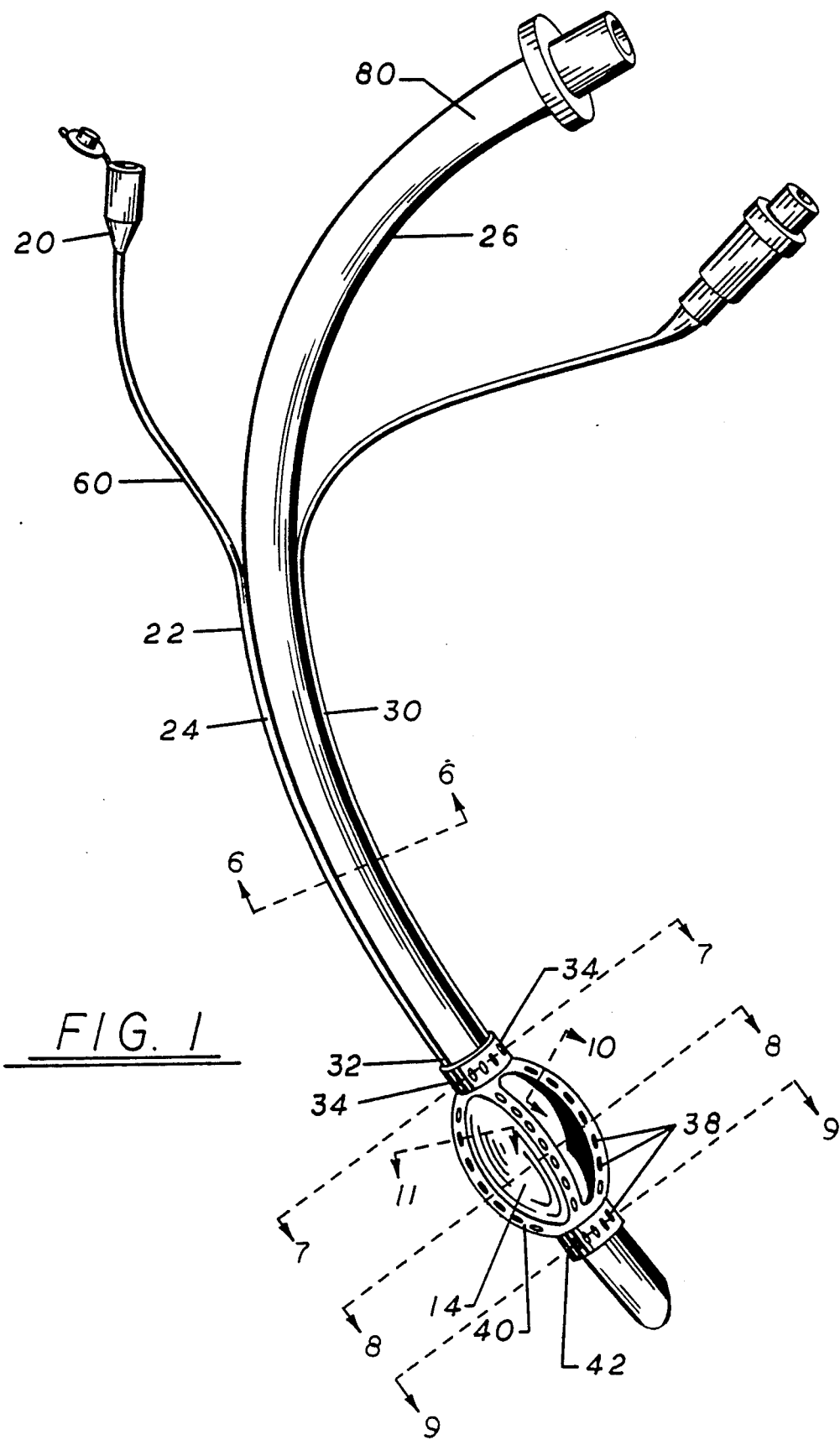
FIG. 1 is a perspective view of the preferred embodiment of the flexible, non-collapsible conduit system invention separable from but combined with a cuffed endotracheal tube, the latter of which in shown in phantom line.
Figure 4:
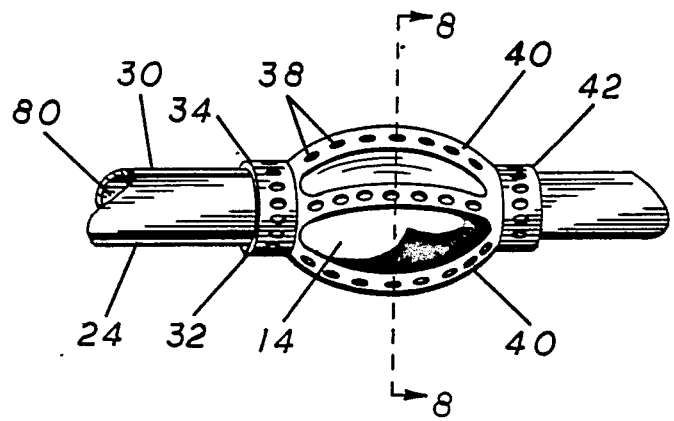
FIG. 4 is a partial view of the conduit system of the present invention showing the flexible, non-collapsible conduit element as incorporated about the standard balloon cuff with the cuff in its inflated disposition.

Referring to FIGS. 1, 2, and 3, the preferred, exemplary embodiment of the invention comprises a system 60 of flexible, non-collapsible conduits for the direct administration of topical medicinal substances (such as for example anesthetic agents) combined with a standard endotracheal tube 80 with an inflatable balloon cuff 14. The integrated combination is shown in FIG. 1, and the standard, prior art, cuffed endotracheal tube by itself is shown in FIG. 3 with the inflatable cuff 14 having fixed proximal and distal collar ends 16 and 18, respectively, that are uninflatable.

Referring further to FIGS. 1, 2, 4, 5, 7, 8, 9, 10 and 11, irrigating system 60 comprises an injection port and tubing 20 connected to the proximal end 22 of an irrigation passage 24 defined in the endotracheal tube wall 26 and diametrically opposed to the inflation passage 30 of the inflatable cuff 14. Distal end 32 of the anesthetic irrigation passage 24 opens orthogonally into a first non-collapsible conduit 34 fixed around the proximal collar end 16 of the inflatable cuff 14.

Outer perforations or openings 38 defined in the outer wall of the proximal, non-collapsible conduit 34 leak topical anesthetic or other medicinal fluid to the adjacent, upper tracheolaryngeal areas when the endotracheal tube and the apparatus of the invention are in their operable locations.

Four, flexible, self-supporting non-collapsible conduit bands 40, each separated from the other annularly by ninety degrees, are orthogonally connected with the first non-collapsible conduit ring 34 and spaced equally around to extend longitudinally and be incorporated into and over the inflatable cuff 14 to orthogonally connect with a second, non-collapsible conduit ring 42 similarly fixed around the distal collar end 18 of the cuff 14. It is noted that the phrase "non-collapsible conduit" means conduit whose lumen is always patent regardless of the position or state of operation of the system.

Outer perforations or openings 38 defined in the outer wall of the distal, non-collapsible conduit 42 leak topical anesthetic or other medicinal fluid to the adjacent, lower tracheal or bronchial area when the endotracheal tube and the apparatus of the invention are in their operable locations.

It is noted that the outer perforations 38 defined in the four flexible non-collapsible longitudinal conduits 40 incorporated into and over the inflatable cuff 14 leak topical anesthetic or other medicinal substance to the tracheal tissue in direct contact with the inflatable cuff 14, tissue which would otherwise be blocked, occluded or compressed by the inflatable cuff 14 without such incorporated conduits 40.

When in use, the cuffed endotracheal tube and integral topical anesthetic irrigation system is inserted through the mouth and into the larynx and trachea, and the cuff is inflated to secure a proper seal to block the system from the esophagus, and to prevent the loss of pulmonary inflation pressure, oxygen or anesthetic gases. A topical anesthetic agent or some other medicinal fluid is introduced into the port and tubing 20 and flows into the passage 24 and into the successive, non-collapsible conduits 34, 40, and 42 to leak respectively therefrom into the blocked areas. This is continued for as long as any convenient time without the need to remove the blocking endotracheal tube, deflate the balloon cuff or deepen the level of anesthesia.

The conduit system of the present invention functions independently of the endotracheal balloon cuff, and may leak anesthetic fluid, under direct control of the operator, regardless of the status of the balloon cuff—inflated or deflated. Cuff pressure, thoracic pressure and fluid pressure remain independent of each other.

Figure 5:
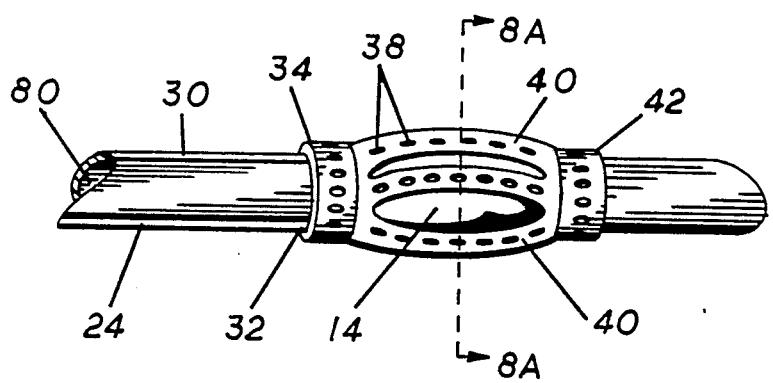
FIG. 5 is a similar view of that portion of the flexible non-collapsible conduit system invention as incorporated about a standard balloon cuff as in FIG. 4 but with the latter in its deflated disposition.
Figure 6:
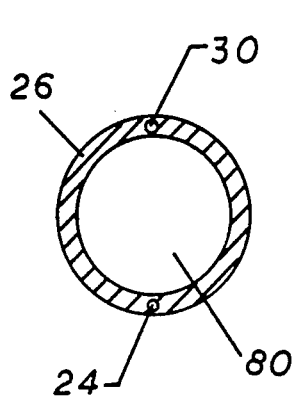
FIG. 6 is a cross-sectional view of the endotracheal tube of FIG. 1 taken along section lines 6—6.
Figure 7:
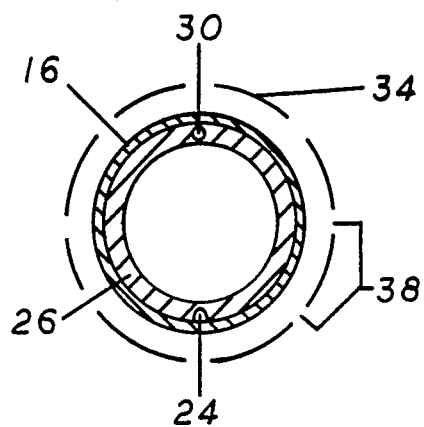
FIGS. 7 and 9 are cross-sectional views similar to FIG. 6 but taken along section lines 7—7 and 9—9, respectively, of FIG. 1.
Figure 8:
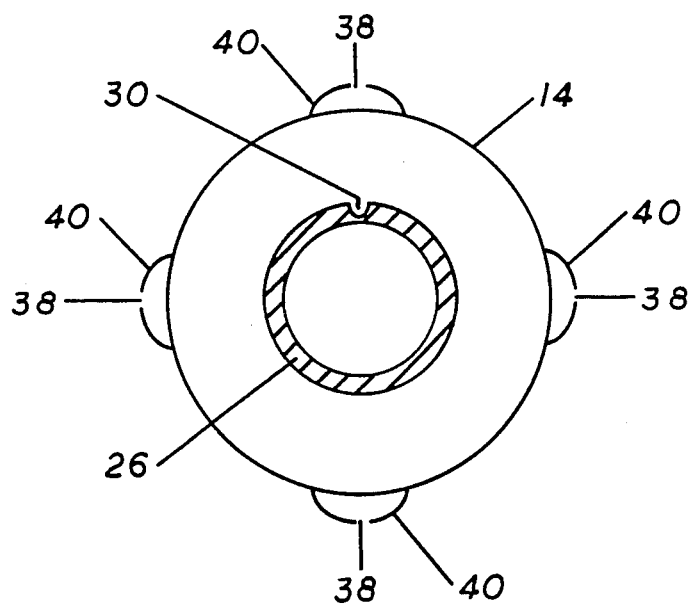
FIG. 8 is a cross-sectional view of the embodiment of FIG. 1 taken along section lines 8—8 (see also FIG. 4).
Figure 8A:
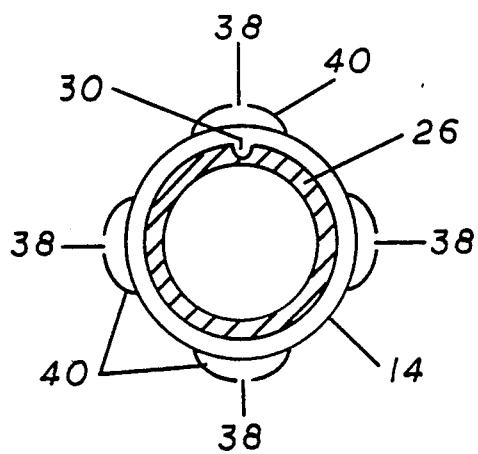
FIG. 8A is a cross-sectional view of the preferred embodiment of FIG. 1 in the deflated condition of FIG. 5, taken along section lines 8A—8A similar to FIG. 8, except with the cuff in the on-distended (deflated) disposition.
Figure 9:
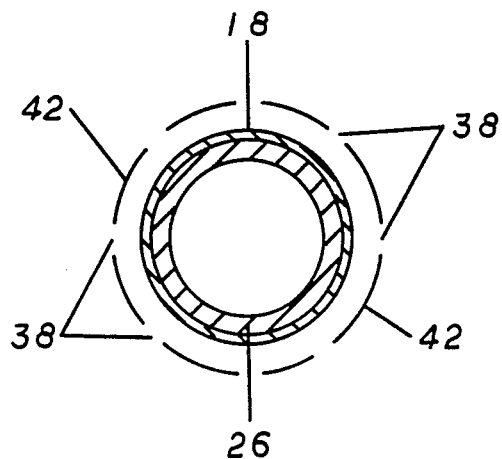
Figure 10:
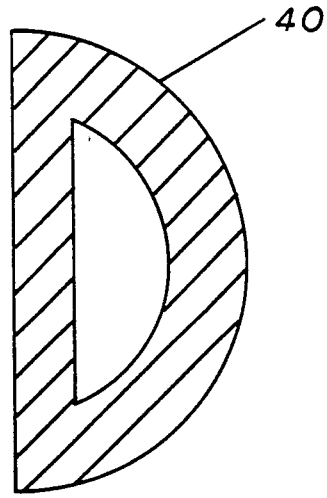
FIG. 10 is a cross-sectional view of one of the flexible, non-collapsible conduits, taken along section lines 10—10 of FIG. 1.
Figure 11:
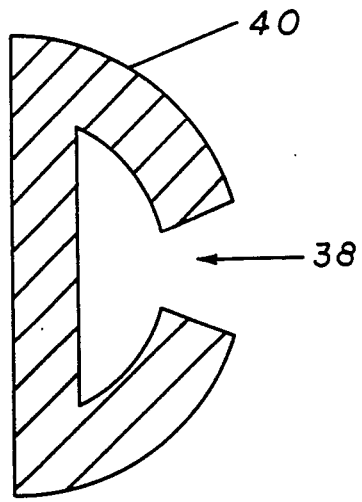
FIG. 11 is a cross-sectional view, similar to FIG. 10, except showing the perforation of the outer wall of the non-collapsible conduit, taken along section lines 11—11 of FIG. 1.

It is noted that, in describing the conduit system 40 as being flexible and self-supporting, the bands 40 can conform to different, increasing diameters as the balloon cuff is inflated, but on the other hand do not completely collapse when the bottom cuff is completely deflated, as for example is shown in FIG. 5. Thus it has somewhat of a semi-rigid but flexible nature.

Figure 12:
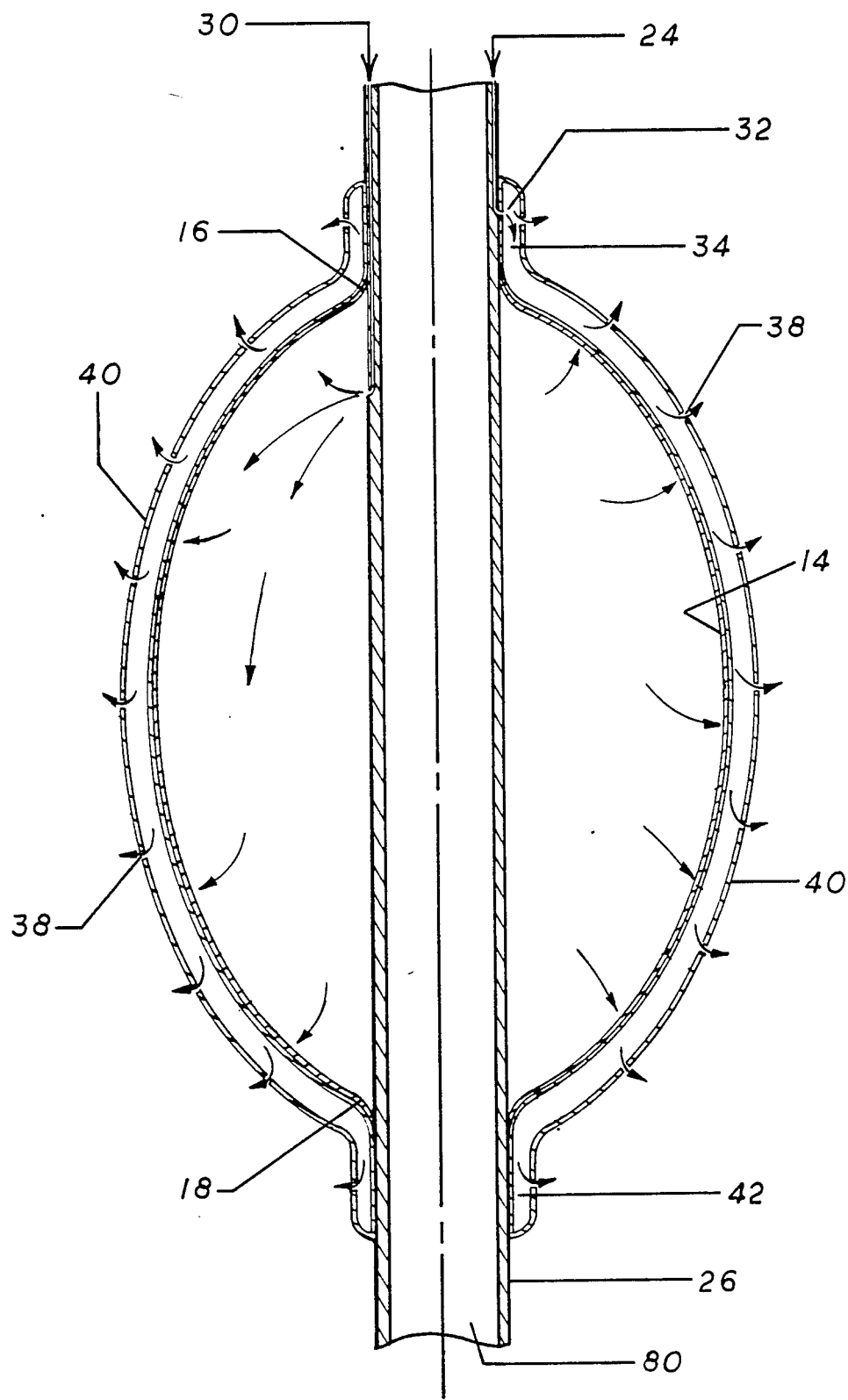
FIG. 12 is a side cross-sectional view of the combined unit of FIG. 1 showing the flow of medical substance(s) and inflation pressure on the balloon-like cuff by means of direction arrows.

The flow of the medical substance(s) through the internal, patent lumens of the conduits 40 of the system of the present invention and the internal inflation pressure in the balloon-like cuff is shown by the direction lines in FIG. 12. It should be understood that the conduit system of the present invention maintains patency regardless of the manipulation of the tube or cuff and is functional in all modes, that is, it remains functional regardless of the state of the ETT. Additionally, the system is serviceable to all the tissues, proximal, around and distal to the inflated ETT. These characteristics are in contrast to the devices of the prior art.

A comparison between some of the different physical characteristics of an exemplary embodiment of the invention and a prior art "Barans" device is present below:

| PRIOR ART "BARANS" DEVICE | EXEMPLARY EMBODIMENT OF INVENTION |
|---|---|
| Thickness of standard endotracheal tube cuff 1/25 millimeter | Self-supporting conduit thickness 1/10 to 1/5 millimeter (thickness of the wall of the device |
| Circumference of standard endotracheal tube cuff approximately 110 millimeters (cross sectional diameter 35 millimeters | Total cross-sectional diameter of self-supporting conduits 8 millimeters (each conduit has a cross-sectional diameter of 2 millimeters) |
| Barans device encircles 100% of the surface area of a standard endotracheal | Self-supporting conduit system on encircles thirteen (13%) percent of the surface area of a |

| PRIOR ART "BARANS" DEVICE | EXEMPLARY EMBODIMENT OF INVENTION |
|---|---|
| tube cuff | standard endotracheal tube cuff (four equally spaced conduits) |
| Standard endotracheal tube is made of polyvinylchloride compound | Self-support conduit system may be made of polyvinylchloride compound or may be made of a silicone compound |
| Barans device (1983) is partially composed of sponge rubber | |
| Total fluid capacity of Barans device - approximately 10 to 12 cc's (cc = cubic centimeter) | Total fluid capacity of self supporting conduit system - approximately 2 to 3 cc's (cc = cubic centimeters) |

Although four equally, peripherally spaced sub-conduits 40 separate annularly ninety degrees are believed to be preferred in the invention, a different number and other spacings (equal or otherwise) are possible. Additionally, although having the sub-conduits 40 extend longitudinally and peripherally over and above the cuff 14 from the two end conduit rings 34, 42, is believed to be preferred, it is possible to incorporate or integrate the conduit system within or internal to the balloon cuff itself. Thus, embodiments of the invention could be provided as a separable, independent device such as is illustrated in FIG. 2 or integrated with the endotracheal tube itself, as may be desired.

Because many varying and different embodiments may be made within the scope of the inventive concept herein taught, and because many modifications may be made in the embodiment(s) herein detailed in accordance with the descriptive requirements of the law, it is to be understood that the details herein are to be interpreted as illustrative and not in a limiting sense.

What is claimed is:

1. A medical system, comprising:
a tubular member;
a pair of annular collar means inserted over said tubular member and fixedly attached to said tubular member in a spaced arrangement on said tubular member for forming a pair of spaced collar means;
an imperforate inflatable annular cuff member disposed over said tubular member between said collar means;
means along said tubular member for communicating with the interior of said cuff member to inflate said cuff member from a first uninflated configuration, to a second configuration having a sealing engagement with the laryngotracheal area of a human body; and
a flexible self-supporting conduit system connected between said collar means and disposed longitudinally over said cuff member;
open passage means in said conduit system when said cuff member is expanded to its second configuration, said open passage means allowing said cuff member to have a constant second inflated configuration to apply a constant pressure on the laryngotracheal area;
a plurality of openings in said conduit system communicating said open passage means with the laryngotracheal area sealingly engaged around said cuff member when said cuff member is expanded to its second configuration;
means along said tubular member communicating with said open passage means for communicating surgical fluid through said open passage means and through said openings into the laryngotracheal area sealingly engaged around said cuff member when said cuff member is expanded to its constant second configuration.

2. A medical system, comprising:
a tubular member;
a pair of annular collar means inserted over said tubular member and fixedly attached to said tubular member in a spaced arrangement on said tubular member for forming a pair of spaced collar means;
an imperforate inflatable annular cuff member disposed over said tubular member between said collar means;
passage means along said tubular member for communicating with the interior of said cuff member for expanding said cuff member from a first uninflated configuration, to a second inflated configuration having a sealing engagement with the laryngotracheal area of a human body;
a plurality of flexible, elongated conduits connected between said collar means and disposed longitudinally over said cuff member, said conduits being spaced around the circumference of said cuff member;
open passage means in said conduits when said cuff member is expanded to its second configuration, said open passage means allowing said cuff member to have a constant second inflated configuration to apply a constant pressure on the laryngotracheal area;
passage means in said collar means in communication with said open passage means in said conduits;
a plurality of openings in said conduits communicating said open passage means with the laryngotracheal area sealingly engaged around said cuff member when said cuff member is expanded to its second configuration; and
passage means along said tubular member communicating with said open passage means in said collar means for communicating surgical fluid to said open passage means and through said openings into the laryngotracheal area sealingly engaged around said cuff member when said cuff member is expanded to its constant second configuration.

3. The medical system of claim 2, wherein said flexible, elongated conduits are expandable from a first configuration in which said cuff is in its first uninflated configuration and said conduits are convexly disposed over said cuff member, to a second configuration wherein said cuff is in its second inflated configuration and said conduits have expanded their convex disposition to an increasing diameter.

4. A method of applying a surgical fluid to the laryngotracheal area, comprising the steps of:
inserting a tubular member into the laryngotracheal area of a human body;
expanding an imperforate, annular cuff member disposed around the tubular member to an inflated configuration wherein the cuff member has sealing engagement with the laryngotracheal area;
maintaining a constant expansion to the cuff member to apply a constant pressure on the laryngotracheal area;
providing a flexible self-supporting conduit system over the annular surface of the cuff member having an open passage means therein when the cuff member is expanded to its inflated configuration;
providing a plurality of openings in the wall of the conduit for communicating the open passage means with the laryngotracheal area sealingly engaged around the cuff member; and
communicating surgical fluid to the laryngotracheal area sealingly engaged around the cuff member when the cuff member is in its inflated configuration by means of the open passage means and the openings in the wall of the conduit system.

5. The system of claim 1, wherein said annular collar means comprises two circular, longitudinally spaced end rings; and said conduit system including a series of longitudinally extending but annularly spaced conduit bands which are extendable out in the radial direction under pressure from the inflating cuff of the endotracheal tube and extend from end-to-end between said rings.

6. The system of claim 5, wherein there are about four of said conduit bands equally spaced annularly about said rings.

7. The system of claim 6, wherein there are four of said conduit bands spaced aparat ninety degrees from each other.

8. The system of claim 5, wherein said band are self-supporting remaining in an outwardly, radially distended disposition spaced from the balloon-like cuff when said cuff is totally deflated.

9. The system of claim 2, wherein said annular collar means comprises two circular, longitudinally spaced end rings; and said elongate conduits including a series of longitudinally extending but annularly spaced conduit bands which are extendible out in the radial direction under pressure from the inflating cuff of the endotracheal tube and extend from end-to-end between said rings.

10. The system of claim 9, wherein there are about four of said conduit bands equally spaced annularly about said rings.

11. The system of claim 10, wherein there are four of said conduit bands spaced apart ninety degrees from each other.

12. The system of claim 9, wherein said band are self-supporting remaining in an outwardly, radially distended disposition spaced from the balloon-like cuff when said cuff is totally deflated.

* * * * *